United States Patent [19]
Demian et al.

[11] Patent Number: 5,795,922
[45] Date of Patent: Aug. 18, 1998

[54] BONE CEMENT COMPOSITION CONTAINING MICROENCAPSULATED RADIOPACIFIER AND METHOD OF MAKING SAME

[75] Inventors: Hany W. Demian, Potomac, Md.; Shalaby W. Shalaby, Anderson, S.C.

[73] Assignee: Clemson University, Clemson, S.C.

[21] Appl. No.: 467,361

[22] Filed: Jun. 6, 1995

[51] Int. Cl.$^6$ .............. B32B 9/00; B32B 5/16; A61K 9/50; A61L 25/00
[52] U.S. Cl. .............. 523/117; 523/116; 428/402.24; 424/419; 524/423; 524/430; 524/560; 524/534
[58] Field of Search .............. 523/117, 116; 524/423, 430, 560; 428/402.24; 424/419

[56] References Cited

U.S. PATENT DOCUMENTS

| | | | |
|---|---|---|---|
| 3,715,331 | 2/1973 | Molner | 523/117 |
| 3,943,063 | 3/1976 | Morishita et al. | 424/419 |
| 4,404,327 | 9/1983 | Crugnola et al. | |
| 4,456,711 | 6/1984 | Pietsch et al. | |
| 4,500,658 | 2/1985 | Fox | 523/117 |
| 4,535,485 | 8/1985 | Ashman et al. | |
| 4,547,390 | 10/1985 | Ashman et al. | |
| 4,617,327 | 10/1986 | Podszun | |
| 4,670,250 | 6/1987 | Baker | 424/419 |
| 4,675,140 | 6/1987 | Sparks et al. | |
| 4,791,150 | 12/1988 | Braden et al. | 523/117 |
| 4,963,151 | 10/1990 | Ducheyne et al. | |
| 5,061,520 | 10/1991 | Hermelin | |
| 5,334,626 | 8/1994 | Lin | |

FOREIGN PATENT DOCUMENTS

| 3018966 | 12/1981 | Germany | 523/117 |
|---|---|---|---|

OTHER PUBLICATIONS

B. Chithabara Thanoo and A. Jayakrishnan, Radiopaque hydrogel microspheres, J. Microencapsulation, 1989, vol. 6, No. 2, 233–244.

B. Chithambara Thanoo and A. Jayakrishnan, Barium sulphate–loaded p(HEMA) microspheres as artificial emboli: preparation and properties, Biomaterials, vol. 11, Sep. 1990, pp. 447–481.

*Primary Examiner*—Andrew E. C. Merriam
*Attorney, Agent, or Firm*—Dority & Manning, P.A.

[57] ABSTRACT

A radiopaque bone cement used to repair bone or other hard tissues is provided. The bone cement is made from combining a composition containing an acrylic powder and a radiopacifier with a corresponding liquid monomer. Prior to being added to the composition, the radiopacifier is microencapsulated with a bone cement compatible material. When combined with the liquid monomer, the bone cement compatible material dissolves releasing the radiopacifier particles into a bone cement matrix. By being microencapsulated, the radiopacifier is prevented from agglomerating in the cement. Instead, the radiopacifier particles become dispersed throughout the bone cement matrix which not only creates a radiopaque cement but also increases the fatigue life of the cement.

25 Claims, 1 Drawing Sheet

Fig. 1

BONE CEMENT COMPOSISTION CONTAINING MICROENCAPSULATED RADIOPACIFIER AND METHOD OF MAKING SAME

BACKGROUND OF THE INVENTION

The present invention generally relates to a radiopaque bone cement and more particularly to a composition used in making a bone cement that contains a microencapsulated radiopacifier. Also included is a method of preparing the composition containing the radiopacifier.

As used in the medical field, a bone cement generally refers to a biocompatible material that can be used to repair damaged or diseased bone or other hard tissues. Specifically, bone cement is used to fill voids or gaps in bones, to affix or anchor an orthopedic implant in a prepared area of the body, or to repair or replace damaged or diseased teeth. Ideally, the bone cement closely assimilates the mechanical characteristics of the hard tissue that the cement is intended to repair or replace.

In most applications, bone cement is made from an acrylic polymeric material. Typically, the bone cement is comprised of two components: a dry or powder component and a liquid component, which are subsequently mixed together to form a resulting cured cement. The dry component of a bone cement system generally includes an acrylic polymer, such as polymethyl methacrylate (PMMA). The PMMA is typically present in the form of small polymer beads, but can also appear in the form of amorphous particles. Regardless, the PMMA powder generally has the consistency of flour.

In addition to the acrylic polymer, a polymerization initiator such as benzoyl peroxide can also be added to the powder component for the purpose of later initiating a free-radical polymerization process. The polymerization initiator can be added as small particles or can be incorporated into the beads made from the polymer.

The liquid component, on the other hand, typically contains a liquid monomer that is mixed with the corresponding acrylic polymeric powder. One example of a liquid monomer is methyl methacrylate (MMA). The liquid component can also contain an accelerator such as an amine (e.g., N,N-dimethyl-p-toluidine). A stabilizer, such as hydroquinone, can also be added to the liquid component to prevent premature polymerization of the liquid monomer.

When the liquid component is mixed with the powder or dry component, initially, the liquid monomer wets the polymeric powder. Since the powder (PMMA) is soluble in the liquid monomer, the solid polymer beads partially begin to dissolve or swell in the liquid monomer. The polymerization reaction starts as soon as the two components are mixed. The amine accelerator reacts with the initiator to form free radicals which begin to link monomer units to form polymer chains. In particular, the liquid monomer and the dissolved portions of the polymer powder are transformed into polymer chains. In the next 2 to 4 minutes, the polymerization process proceeds changing the viscosity of the mixture from a syrup like consistency (low viscosity) into a dough-like consistency (high viscosity).

In this state, the bone cement is applied to a prepared area of the body where it is to be used. Ultimately, further polymerization and curing occur until the cement is fully hardened.

Typically, it takes anywhere from about 5 minutes to about 20 minutes for the bone cement to fully cure after the two components are mixed. Since the polymer beads only partially dissolve during mixing, the resulting solid cement includes a dispersion of polymeric beads contained in a matrix of the acrylic polymer.

Perhaps the most commonly used application for bone cement is in the fixation of prosthetic devices. Prosthetic devices are artificial devices used to replace or strengthen a particular part of the body. When implanting a prosthesis, first a receiving site or cavity is prepared in an adjoining bone. In particular, the bone can be cut and reamed out in order to accommodate the prosthesis. A bone cement is then mixed and placed in the receiving site or cavity. A prosthesis is positioned in the bone cement and the bone cement is hardened affixing the prosthesis to the bone.

The above process for implanting a prosthetic device is generally accepted within the art and has proven to be a successful process for repairing or replacing damaged bones and the like. Prosthetic devices, however, can be prone to loosen within the bone cavity over time. In particular, the acrylic bone cement has been universally considered the weakest link in the implant design. Most bone cements are neither as strong nor as flexible as bone tissue. Consequently, the bone cement can break away from the prosthesis, can fracture or can develop fatigue cracks when exposed to repeated loads.

Because problems can develop in the bone cement mantle or bed surrounding a prosthesis, it is important that the condition of the implant product be monitored after surgery. However, bone cement, like most polymers, is relatively radiolucent, meaning that the bone cement is transparent to X-rays. Consequently, in order to inspect the bone cement mantle postoperatively, radiopacifiers are commonly added to the dry component of a bone cement system in a sufficient amount to give the resulting bone cement the necessary radiopacity for examination by X-rays.

Unfortunately, radiopacifiers, such as barium salts and certain metal oxides, when added to bone cement, tend to reduce the mechanical properties of the cement. Radiopacifiers, which have a higher density and polarity than the polymeric material they are mixed with, tend to collect together and clump or agglomerate in the bone cement. These agglomerates have been shown to act as stress concentration sites and have been shown to decrease the ultimate flexural strength, ultimate tensile strength, fatigue strength, as well as the fracture toughness of the cement.

Due to these deficiencies, many of those skilled in the art have attempted to improve the mechanical properties of radiopaque bone cements. For instance, in U.S. Pat. No. 4,500,658 to Fox, a radiopaque acrylic resin is disclosed. Specifically, a radiopaque inorganic pigment is disbursed in the polymer beads that are incorporated into the bone cement. The polymer beads incorporating the pigment are formed through suspension polymerization.

U.S. Pat. No. 4,791,150 to Braden, et al. also teaches incorporating particles of an opacifier into the polymer beads. By incorporating the opacifier particles into polymer beads, the particles will remain trapped within the beads during formation of the bone cement, preventing the particles from forming agglomerates in the polymer matrix.

Other bone cement materials containing radiopacifiers are disclosed in U.S. Pat. No. 4,547,390 to Ashman, et al.; U.S. Pat. No. 4,535,485 to Ashman, et al.; U.S. Pat. No. 4,456,711 to Pietsch, et al.; U.S. Pat. No. 4,404,327 to Cruganola; and U.S. Pat. No. 3,715,331 to Molnar.

However, various features and aspects of the present invention remain absent from the prior art. Specifically, the prior art teaches incorporating radiopacifiers into the polymer beads. To the contrary, the present invention is directed to releasing a pre-microencapsulated radiopacifier into the polymer/monomer matrix as it cures. The radiopacifier is microencapsulated for preventing the material from clumping or forming agglomerates prior to or during curing. It has been found, that by dispersing the radiopacifier, as such, within the polymer matrix, the radiopacifier can be used to improve the fatigue life of the cement.

SUMMARY OF THE INVENTION

The present invention recognizes and addresses the foregoing disadvantages and others of prior art constructions and methods.

Accordingly, it is an object of the present invention to provide an improved bone cement composition containing a radiopacifier.

It is another object of the present invention to provide a bone cement composition containing a microencapsulated radiopacifier.

Another object of the present invention is to provide an improved method of preparing a composition used to make bone cement, wherein the composition contains a radiopacifier.

Still another object of the present invention is to provide a bone cement composition containing a radiopacifier that increases the fatigue life of a bone cement made therefrom.

These and other objects of the present invention are achieved by providing a radiopaque composition for combining with a liquid monomer to produce a bone cement. The composition includes an acrylic powder capable of polymerizing and ultimately hardening when combined with the corresponding monomer. The composition further includes a radiopacifier that is microencapsulated within a bone cement compatible polymer. When combined with the liquid monomer, the bone cement compatible polymer dissolves dispersing the radiopacifier throughout the resulting bone cement matrix. Generally, the radiopacifier is present within the composition in an amount sufficient to make the resulting bone cement radiopaque.

Microspheres of the microencapsulated radiopacifier generally have a diameter between about 1 micron to about 100 microns. The radiopacifier can be present within each microsphere in an amount from about 15 percent to about 70 percent by weight. The bone cement compatible polymer used to microencapsulate the radiopacifier can be polymethyl methacrylate or copolymers thereof. When using polymethyl methacrylate, the polymer can have a weight average molecular weight from about 30,000 to about 500,000 daltons. As used herein, all given molecular weights are as would be determined by gel permeation chromatography.

The radiopacifier microencapsulated within the polymer can be a metal oxide, a barium salt, or a bismuth glass. The microspheres can then be added to the composition such that the radiopacifier is present within the composition in an amount from about 5 percent to about 30 percent by weight.

These and other objects are also achieved by providing a method of preparing a composition used to make bone cement. The composition is for combining with a liquid monomer for producing a resulting bone cement used in repairing and replacing bones, teeth and other hard tissues. The method includes the steps of first microencapsulating a radiopacifier in a wall forming polymer to form radiopaque microspheres. Next, the microspheres are combined with an acrylic powder to form a dry mixture. The microspheres are added to the acrylic powder in an amount sufficient to make a resulting bone cement radiopaque. When the mixture is contacted with a liquid monomer in order to form a resulting cement, the wall forming polymer dissolves releasing the radiopacifier into the curing bone cement matrix. In a preferred embodiment, the wall forming polymer is an acrylic powder such as polymethyl methacrylate or copolymers thereof.

Besides causing the dispersion of the radiopacifier throughout the bone cement, the polymer coating surrounding the radiopacifier also facilitates wetting of the radiopaque particles with the liquid monomer. Enhanced wetting of the radiopacifier leads to less air entrapment in the resulting cement and higher intimacy between the radiopaque particles and the polymer matrix.

In order to microencapsulate the radiopacifier, the wall forming polymer can be first combined with the radiopacifier and a solvent. The wall forming polymer dissolves in the solvent while the radiopacifier does not. The solvent mixture is then blended with an aqueous solution to form an emulsion. The solvent is then evaporated from the emulsion thereby forming small microspheres containing a microencapsulated radiopacifier. The microspheres are then separated from the remaining aqueous solution and dried.

Other objects, features and aspects of the present invention are discussed in greater detail below.

BRIEF DESCRIPTION OF THE DRAWINGS

A full and enabling disclosure of the present invention, including the best mode thereof, to one skilled in the art, is set forth more particularly in the remainder of the specification including reference to the accompanying figure in which.

Repeat use of reference characters in the present specification and drawing is intended to represent same or analogous features or elements of the invention.

DETAILED DESCRIPTION OF THE PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to a bone cement composition containing a radiopacifier. The composition is for mixing with a liquid monomer in order to produce a resulting radiopaque bone cement. Specifically, the composition contains a radiopacifier that has been microencapsulated in a bone cement compatible material. The microencapsulated radiopacifier is then mixed with a polymeric acrylic powder for producing the dry component of a bone cement system.

As opposed to incorporating a radiopacifier into a polymer bead, the bone cement compatible material encasing the radiopacifier of the present invention dissolves when mixed with a corresponding liquid monomer releasing and dispersing the radiopacifier throughout a curing bone cement matrix. By being microencapsulated, the radiopacifier is prevented from clumping and forming agglomerates within the bone cement composition and within the resulting bone cement. In fact, by dispersing the radiopacifier throughout the bone cement matrix, the fatigue life of the cement is increased.

As used herein, a microencapsulated radiopacifier is much different in structure than a solid polymer bead that has radiopaque particles incorporated into it. Specifically, a polymer bead is made from a solid polymer. The polymer is solid and continuous throughout the bead. The microencapsulated radiopacifier of the present invention, on the other hand, only includes a thin outer coating of polymer. The coating is capable of completely dissolving during mixing with a liquid monomer.

Microencapsulation also enhances contact between the radiopacifier and the curing cement. Specifically, it is believed that by dissolving the outer polymeric coating of the microencapsulated radiopacifier during mixing with the liquid monomer, the radiopaque particles are completely wet by the liquid monomer. When dispersed into the curing bone cement, the radiopaque particles maintain intimate contact with the surrounding polymer matrix. When the radiopacifier is uncoated, air pockets and voids can form in the bone cement. The present invention prevents against such adverse results.

The particular radiopacifier used in the present invention may vary depending upon the circumstances and the particular application. For instance, factors to consider in choosing a radiopacifier include the final effect that is desired, the ability to microencapsulate the material due to the size of the particles of the radiopacifier, and the costs involved. Radiopacifiers that may be used in the present invention include, but are not limited to, barium salts, such as barium sulfate, barium fluoride, and barium polyacrylate; metal oxides, such as titanium dioxide, zirconium oxide, chromium oxide, and zinc oxide; bismuth glass; and mixtures thereof. In a preferred embodiment, either barium sulfate, zirconium dioxide or a bismuth glass is used.

Once a proper radiopacifier is selected, in accordance with the present invention, the radiopacifier is microencapsulated prior to being combined with a dry component of a bone cement system. Microencapsulation is a process by which a small particle or particles are encapsulated and coated by a second material. Preferably, the radiopacifier particles are microencapsulated using a solvent evaporation process.

In a solvent evaporation scheme, two immiscible phases, an organic phase and an aqueous phase, are combined together. Next, a solvent contained in the organic phase is evaporated which leads to the formation of hardened microspheres.

When using the solvent evaporation process to microencapsulate a radiopacifier, the organic phase is prepared by combining the radiopacifier with a wall-forming polymer and a solvent. The wall-forming polymer selected must be insoluble in the aqueous phase but soluble in the solvent. Also, since the wall-forming polymer is used to encapsulate the radiopacifier, the wall-forming polymer must also be bone cement compatible. As used herein, bone cement compatible means that the wall-forming polymer will not interfere but will intermix with a bone cement during curing and will not adversely effect any of the mechanical properties of the cement. Preferably, the wall-forming polymer is made from the same polymer that is used to make the bone cement. For instance, the wall-forming polymer used in the present invention can be polymethyl methacrylate or a copolymer thereof.

The polymer solvent selected for blending with the wall-forming polymer and the radiopacifier must be water immiscible and volatile, such that it has a lower boiling point than water. Solvents that can be used in the microencapsulation process of the present invention include methylene chloride, chloroform, ethylene chloride and benzene. The solvent selected must be capable of dissolving the wall-forming polymer without dissolving the radiopacifier.

When forming the organic phase, the concentration of the wall-forming polymer in the solvent will vary depending upon the particular application. Generally, the concentration of polymer in the solvent can be anywhere from about 3 percent to about 50 percent. Likewise, the amount of radiopacifier added to the organic phase will vary. Typically, the wall-forming polymer to radiopacifier ratio in the solution can range from 2:1 to 1:2 respectively. The radiopacifier added to the solution should be reduced to the smallest possible particle size.

The aqueous phase, on the other hand, is primarily made up of water. Alternatively, an emulsifier can be added to prevent coalescing and agglomeration of the organic phase when the two solutions are mixed. Hydrophilic polymers such as gelatin and polyvinyl alcohol can be used as emulsifiers. The pH of the aqueous phase can be adjusted to enhance the performance of the emulsifier. Also, in an alternative embodiment, the radiopacifier can be added to the aqueous phase instead of, or along with, addition to the organic phase.

After preparing the organic phase and the aqueous phase, the two phases are mixed to form an emulsion. After thoroughly mixing the two phases, the emulsion may be heated while stirring in order to evaporate the solvent. As the solvent is evaporated, the wall-forming polymer hardens around the radiopacifier particles to form small microspheres. After the solvent has substantially evaporated, the resulting aqueous solution can be filtered in order to separate out the microencapsulated radiopacifier. The microspheres can then be allowed to dry before incorporation into a bone cement system.

When forming microencapsulated radiopacifiers in accordance with the present invention, preferably the resulting microspheres are small in size. The smaller the size of the microspheres and the thinner the thickness of the coating, the more likely the coating around the radiopacifier will dissolve when contacted with a liquid monomer. Although dependent upon the materials used, the diameter of the resulting microspheres should be between about 1 micron to about 250 microns. Preferably, the diameter should be between about 1 micron to about 100 microns and most preferably between about 5 microns to about 80 microns. The radiopacifier should be completely encapsulated within the wall-forming polymer. Also, the radiopacifier should make up a substantial portion of the microsphere. For instance, when using barium sulfate, the radiopacifier should account for from between about 15 percent to about 70 percent by weight of the microsphere, and preferably about 55 percent.

The thickness of the coating can also vary. Again, very thin coatings are preferred in order to ensure complete dissolvability when contacted with a monomer. Also, coatings made from lower molecular weight polymers will dissolve faster than those made from higher molecular weight polymers. Thus far, it has been found that coatings between 1 and 10 microns thick are preferred. In general, the coating thickness should be less than 25 microns and less than ½ the diameter of the microsphere itself.

Further, a single radiopacifier particle, or, alternatively, a group of particles can be incorporated into each microsphere. For instance, barium sulfate particles typically have a diameter of less than 1.5 microns with a majority of particles having a diameter less than one micron. As such, a group of barium sulfate particles can be microencapsulated according to the present invention while remaining within the above-described diameter ranges. Of course, the amount of radiopacifier incorporated into each individual microsphere should be less than an amount that will cause adverse effects in the resulting bone cement.

The microspheres that are formed do not agglomerate when mixed with a bone cement system but instead uniformly disperse the radiopacifier throughout the resulting bone cement matrix. In a preferred embodiment, the wall-forming polymer is a bone cement polymer such as polymethyl methacrylate, a copolymer thereof or a rubber modified PMMA. When using a bone cement polymer, preferably the microspheres are constructed such that the polymer coating will virtually dissolve when contacted with a corresponding liquid monomer when forming the bone cement. When the coating is dissolved, the radiopacifier is released and uniformly dispersed into the forming bone cement matrix. Preferably, the radiopacifier is dispersed when the bone cement composition has reached a dough like consistency. Because of the rapid increase in viscosity of the bone cement during curing, the radiopacifier particles are prevented from clumping or agglomerating within the polymer mass leading to uniform dispersion.. Further, the polymer coating has been found to enhance the contact between the radiopacifier and the curing cement.

Consequently, the resulting hardened bone cement contains a polymer matrix having small radiopacifier particles dispersed uniformly therethrough. A high intimacy is also achieved between the polymer matrix and the particles. When dispersed in the bone cement matrix, the radiopacifier does not adversely affect the mechanical properties of the bone cement but instead increases the fatigue life of the cement. It is hypothesized that the radiopacifier effectively increases the resistance of the cement to crack propagation. In particular, it is believed that propagating cracks are redirected around the uniformly dispersed radiopaque particles. This phenomenon causes more energy to dissipate, slowing the crack propagation rate. Ultimately, the radiopacifier becomes capable of blunting a crack that is propagating through the cement.

Figure 1:
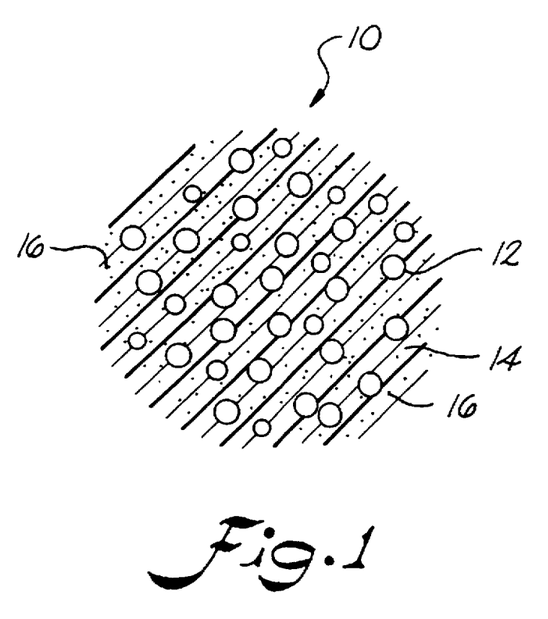
FIG. 1 is schematic diagram of a cured bone cement made in accordance with the present invention.

Referring to FIG. 1, a schematical diagram of a bone cement generally 10 is shown. The diagram is provided in order to more clearly illustrate the present invention in a simplified manner. As shown, bone cement 10 includes a bone cement matrix 14. Dispersed throughout matrix 14 are solid polymer beads 12 which do not completely dissolve during the polymerization process. The beads reinforce the matrix of the cement. In accordance with the present invention, bone cement 10 also includes a radiopacifier 16 evenly dispersed throughout bone cement matrix 14. As shown, the coating used to microencapsulate radiopacifier 16 dissolves during curing of the bone cement releasing the radiopacifier throughout the matrix. The small particles of radiopacifier 16, therefore, do not agglomerate within the matrix. By remaining in small discrete particles, radiopacifier 16 not only creates a radiopaque composition but also increases the fatigue life of the bone cement.

When combining the microspheres with a bone cement system, preferably the microencapsulated radiopacifier particles are mixed with the powder component prior to cement formation. The microspheres should be added to the bone cement in an amount sufficient to make the resulting cement radiopaque. As used herein, a radiopaque bone cement is a bone cement containing a radiopacifier in an amount sufficient to make the cement opaque to X-rays.

When using barium sulfate as the radiopacifier, preferably the microspheres are added to the bone cement such that the resulting bone cement contains from about 5 percent to about 30 percent by weight of the radiopacifier. In most preferred embodiments, the barium sulfate is present in an amount from about 5 percent to about 20 percent by weight. The amount of radiopacifier can be increased or decreased in order to increase the radiopaque properties of the resulting bone cement and/or to increase the fatigue life of the cement.

When using polymethyl methacrylate as the wall-forming polymer, preferably the microspheres are incorporated into the powder component of the bone cement composition. In addition to the large quantity of polymethyl methacrylate contained in the powder component, the powder composition also contains a polymerization initiator such as benzoyl peroxide. The initiator can either be contained within or on the solid polymer beads, can be in a residual form or can be added as an additional powder to the dry component of the bone cement. Generally, the radiopaque microspheres can represent up to about 50% of the total weight of the powder component. Additional components can also be present within the powder composition without effecting the performance of the radiopacifier.

The present invention may be better understood with reference to the following examples. However, the following examples are provided for purposes of illustration only and are not intended to limit the invention to the particular materials and parameters disclosed.

EXAMPLE NOS. 1–19

The following examples, illustrate a process for microencapsulating a radiopacifier for use in a bone cement composition. Specifically, the radiopacifier was encapsulated using a solvent evaporation process. The radiopacifier selected was barium sulfate which was encapsulated in a coating of polymethyl methacrylate. The polymethyl methacrylate served as the wall-forming polymer in the solvent evaporation process.

Specifically, polymethyl methacrylate having different molecular weights were obtained from various sources. The polymethyl methacrylate compositions tested were SIMPLEX P obtained from Howmedica, Inc. in Rutherford, N.J.; PALACOS R obtained from Smith & Nephew Richards, Inc. in Memphis, Tenn.; HFI-7(rubber modified PMMA to toughen the polymer) obtained from Rohm & Haas in Philadelphia, Pa.; and a low molecular weight polymethyl methacrylate was obtained from POLYSCIENCE in Warington, Pa. The barium sulfate was obtained from MALINCKRODT in Paris, Ky.

Table I below summarizes the results of using various starting materials and concentrations to microencapsulate barium sulfate in polymethyl methacrylate using a solvent evaporation process. During the process, the solvent used was chloroform while polyvinyl alcohol (PVA) (molecular weight 85,000–114,000) was used as an emulsifier. The following procedure exemplifies the process steps used to form the various microspheres listed in the table. In a solvent evaporation procedure, two immiscible phases (an organic phase and an aqueous phase) are formed and then combined together by a high speed stirrer during which the microspheres are formed. Next, the solvent is evaporated for hardening the microspheres.

In examples 11–16, the organic phase was prepared by dissolving 20 grams of polymethyl methacrylate in 90 ml of chloroform (22 percent polymer concentration). Fifteen grams of barium sulfate was added to the polymer solution (4:3 ratio of polymer to barium sulfate) and the resulting mixture was sonicated for 2.5 hours in a 20° C. water bath.

The aqueous phase was prepared by dissolving 2.5 grams of polyvinyl alcohol in 500 ml of water. The aqueous solution was mixed by a magnetic stir/heat plate for 2 hours at a temperature between about 34° to about 37° C.

After preparing the organic phase and the aqueous phase, the phases were combined to form an emulsion. Specifically, the aqueous phase was first introduced into a glass reactor followed by the organic phase. A high-speed stirrer was used to form the emulsion of the two immiscible phases. Agitation at approximately 1,125 rpms for 2 hours at ambient pressure and temperature was followed by 20 to 24 hours of continuous mixing at the same speed and at reduced pressure (4 in. Hg) to evaporate the chloroform. After the solvent had evaporated, the newly formed microspheres were filtered and then sieved through a 25 micron sieve and allowed to air dry. The microspheres were then placed in a 20 in. Hg vacuum oven at 60° C. for complete drying.

spheres. The micrographs were scanned into a MacIntosh computer using APPLE SCAN. Using IMAGE BIOE, measurement of the legend bar was calibrated in microns for a designated picsal number and a value was assigned. The diameter of each microsphere was then recorded.

For light microscopy, a sample was placed on a slide in a suspension of water and a cover slide was placed over the sample. The slide was then placed in a light microscope. A micrometer was used to calibrate the eye piece for measurement of the microspheres. Ten grams of sample were taken for each size range and average particle size was determined for each gram.

The results are summarized as follows:

TABLE I

CHARACTERISTICS OF PMMA MICROSPHERES CONTAINING BARIUM SULFATE

| Example No. | Polymethyl Methacrylate Source | Molecular Weight (dalton) | Polymer Concentration (%) | Polymer to Barium Sulfate Ratio | Barium Sulfate in Microspheres (weight %) | Avg Size & Size Range of Microspheres (um) |
|---|---|---|---|---|---|---|
| 1 | Polyscience | 32,226 | 33.3 | 2:1 | 22.8 | 16.7 (7–30) |
| 2 | | | 33.3 | 2:1 | 16.9 | 62.4 (22–90) |
| 3 | Simplex-P | 155,628 | 5.5 | 1:1 | 48.4 | 21.8 (10–30) |
| 4 | | | 12.5 | 1:1 | 46.6 | 23.5 (12–50) |
| 5 | | | 20.0 | 1:1 | 42.5 | 26 (6–50) |
| 6 | | | 3.5 | 1:1 | 53.4 | 20 (5–30) |
| 7 | | | 12.5 | 1:1 | 49.8 | 37 (20–60) |
| 8 | Palacos R | 462,128 | 18 | 4:3 | 22.5 | 107.4 (35–160) |
| 9 | | | 20 | 4:3 | 18.1 | 130.3 (49–250) |
| 10 | | | 7.8 | 1:2 | 45.1 | 64.9 (22–110) |
| 11 | HFI-7 | 86,304 | 22 | 4:3 | 36.1 | 55.2 (30–70) |
| 12 | | | 22 | 4:3 | 37.9 | 52.4 (30–70) |
| 13 | | | 22 | 4:3 | 35.2 | 44.8 (22–70) |
| 14 | | | 22 | 4:3 | 37.9 | 36.6 (10–80) |
| 15 | | | 22 | 4:3 | 36.1 | 56.5 (30–80) |
| 16 | | | 22 | 4:3 | 35.2 | 57.1 (35–70) |
| 17 | | | 11 | 2:3 | 56.0 | 34.6 (12–60) |
| 18 | | | 11 | 2:3 | 56.3 | 37.25 (12–60) |
| 19 | | | 11 | 2:3 | 56.2 | 32 (12–60) |

Thermogravimetric analysis (TGA), differential scanning calorimetry (DSC), scanning electron microscopy (SEM) and light microscopy (LM) were used to characterize and evaluate the formed microspheres. Specifically, thermogravimetric analysis was used to quantatively determine how much barium sulfate was encapsulated in the microspheres. Scanning electron microscopy was used to characterize the morphology and diameter of the microspheres and the thickness of the coating, while light microscopy was used to determine the average size of the microspheres.

Thermogravimetric analysis was performed using Model No. 953 instrument marketed by DuPont. To run the test, a 25 to 30 mg sample of microspheres were placed in a platinum pan. While in a nitrogen environment, the temperature was raised 10° C. per minute to 600° C. The polymethyl methacrylate was pyrolized and an associated weight loss was detected. Barium sulfate, an inorganic salt, was unaffected by the change of temperature. Thermalgravimetric analysis thermograms depicting percent weight versus temperature were used to determine percent incorporation of barium sulfate in the polymer microspheres.

A JELO JSM-IC 848 scanning electron microscope was used to obtain scanning electron micrographs of the micro- As shown in Table I, several process parameters were varied in order to study their influence on the final characteristics of the microspheres formed. In particular, the following factors were studied: (1) concentration of wall-forming polymer in solvent; (2) ratio of barium sulfate to polymethyl methacrylate by weight in solvent; and (3) molecular weight of wall-forming polymer. Besides these factors, it was also discovered that the mixing shear rate and time of mixing of the emulsion had an influence on microsphere formation.

Generally, higher concentrations of the wall-forming polymer in the solvent caused a reduction in the weight percentage of barium sulfate incorporated into the microspheres. Similarly, a higher ratio of wall-forming polymer to barium sulfate in the solvent also resulted in a reduced amount of barium sulfate incorporated into each microsphere.

As discussed above, a principal goal of the present invention is to produce and use a microsphere with a thin coating of polymer that will completely dissolve when placed in a curing bone cement. As such, microspheres that have thinner coatings, have smaller diameters and incorporate higher percentage amounts of radiopacifier particles are preferred.

With respect to the molecular weight of the polymethyl methacrylate used in the process, generally, a lower molecular weight resulted in microspheres with a smaller diameter. In addition, a lower molecular weight material (PMMA) is generally known to be more soluble in the liquid monomer when compared to a higher molecular weight material (PMMA). As such, in most applications, a lower molecular weight polymer is preferred. However, higher molecular weight polymers are generally stronger materials. As such, higher molecular weight polymers are generally more preferred in a bone cement composition.

With respect to polymer concentration in the solvent, it was determined that thinner polymer coatings were produced at lower concentrations of polymer. In particular, polymer concentrations at approximately 11% were preferred. The thickness of the polymer coating was determined using scanning electron microscopy of smashed microspheres. At 11% polymer concentration, the coating thickness was between about 1 to about 5 microns. As discussed above, preferably the coating is less than about 25 microns thick.

With respect to mixing shear rate and time of mixing of the emulsion, it was discovered that higher shear rates and longer mixing times resulted in less barium sulfate being encapsulated into each polymer microsphere.

To summarize the results in Table I, microspheres containing barium sulfate ranged in size from about 5 microns to about 250 microns. The formed microspheres were almost perfectly spherical in shape and the surface morphology showed that the barium sulfate was indeed present within the core of the sphere and completely coated by a thin film of polymer. The weight percentage of barium sulfate incorporated into the microspheres varied between about 16 percent to about 56 percent.

EXAMPLE NO. 20

After microencapsulating the barium sulfate as described in Examples 17–19, the microencapsulated radiopacifier was mixed with the dry component of a bone cement system. A corresponding bone cement was then mixed, cured and transferred to a mold in order to produce various tests specimens. The specimens were then used to test the mechanical properties of the cement. A commercial radiolucent bone cement and a commercial radiopaque bone cement were similarly prepared and tested in order to compare the properties of the various cements.

During curing, random samples of the curing cement containing the microencapsulated radiopacifier were separated and analyzed. Using light microscopy, it was verified that the polymer coating surrounding the radiopaque particles completely dissolved.

The bone cements used in the following tests were SIMPLEX-P radiopaque cement and SIMPLEX-P radiolucent cement. In studying the effects of microencapsulating a radiopacifier, the microencapsulated barium sulfate as produced in Examples 17–19 were added to the SIMPLEX-P radiolucent cement. The following table lists the ingredients present in the SIMPLEX-P cements.

TABLE II

COMPONENTS OF SIMPLEX-P BONE CEMENT SYSTEMS

| Type | Powder Given as Percent By Weight | Monomer Given as Percent By Volume |
|---|---|---|
| Radiopaque Simplex-P | PMMA; MMA-Styrene copolymer; 75% barium sulfate 10% w/w benzoyl peroxide 1–1.9% w/w; | MMA 97.4% v/v; hydroquinone 75 ± 15 ppm; N,N-dimethyl-p-toluidine 2.6% v/v |
| Radiolucent Simplex-P | PMMA; MMA-Styrene copolymer; 75% w/w benzoyl peroxide 1–1.9% w/w | MMA 97.4% v/v; hydroquinone 75 ± 15 ppm; N,N-dimethyl-p-toluidine 26% v/v |

For the following tests, microencapsulated barium sulfate was added to radiolucent SIMPLEX-P powder in an amount so that the resulting powder contained 10 percent by weight barium sulfate. Specifically, 1.2 grams of microspheres (56% wt barium sulfate) were added to 32.8 grams of radiolucent SIMPLEX-P. An additional amount of benzoyl peroxide (in powder form) was also added to the powder when the microspheres were added. The additional benzoyl peroxide was added in order to maintain the level of benzoyl peroxide within the resulting powder at approximately 1 percent by weight.

In preparing the test specimens, the powder and liquid components of the bone cement systems were combined using a centrifugation mixing procedure. During this procedure, a DuPont centrifuge RC5 with a GSA rotor was used. The internal temperature of the centrifuge was placed at 4° C. A 20 ml ampule of liquid monomer was chilled in ice from 2° to 5° C. A 40 g sample of cement powder was then placed in a 600 ml polypropylene beaker. The chilled monomer was added to the powder in the beaker. The cement was hand-mixed with a stainless steel spoon for 30 to 40 seconds.

Quickly, the mixture was transferred into a 60 cc syringe which included a nozzle having a 1.1 cm diameter. A rubber stopper was plugged into the opening of the syringe and the syringe was centrifuged for 3 minutes at 3,000 rpms. The rubber stopper was removed and the curing cement was pushed through the syringe while still deformable.

The cement was placed into aluminum molds designed for tensile and fatigue testing. The test specimens were air cured at 75° to 78° F. for a period of 2 weeks to 2 months before mechanical testing.

Mechanical testing of the cements included tensile and notched fatigue testing to compare SIMPLEX-P radiopaque and radiolucent controls with that of the new cement containing a microencapsulated radiopacifier. Tensile tests followed ASTM standard D 638 while a notched fatigue test was developed to compare the fatigue life of the cements.

Tensile Testing

For tensile tests, ASTM D 638-91 type V specimens were fabricated from the 3 cements using an aluminum mold. Specifically, the following table lists the various dimensions of the specimens that were tested.

TABLE III

DIMENSIONS FOR TENSILE TEST SPECIMENS

| Dimension | Length (MM) | (IN) |
|---|---|---|
| Width of narrow section = | 3.2 | 0.13 |
| Width of Ends = | 9.5 | 0.4 |
| Length Overall = | 63.5 | 2.5 |
| Gage Length = | 7.6 | 0.3 |
| Thickness = | 3.3 | 0.1 |
| Radius of Curve = | 12.7 | 0.5 |

All tensile tests were carried out on an 1125 Instron testing machine using an extensometer (Interlaken Tech Model 3542-0050-005). The specimens were tested at 70° F. and the crosshead speed was 2 mm/min. as suggested by ASTM. A tensile force vs. cross-head displacement curve was converted to a stress-strain curve using the extensometer. Young's modulus of elasticity (E) was computed from the slope of the least squares fit straight line made through the steepest linear region of the stress-strain curve. The ultimate tensile strength was calculated from the chart recorder. The following results were obtained.

TABLE IV

TENSILE STRENGTH TEST RESULTS

| Sample | Number Of Samples | Average Ultimate Tensile Strength (MPa) | Average Modulus of Elasticity (MPa) |
|---|---|---|---|
| Radiolucent | 6 | 60.4 | 3621.3 |
| Radiopaque | 24 | 54.7 | 3446.4 |
| 10% Microsphere | 6 | 53.2 | 3320.0 |

As shown in Table IV, the ultimate tensile strength and the modulus of elasticity for the radiopaque control and for the bone cement containing the microencapsulated radiopacifier were lower than for the radiolucent control. However, use of the microencapsulated radiopacifier did not significantly adversely effect the ultimate tensile strength or the modulus of elasticity of the resulting cement when compared to the radiopaque control.

Fatigue Testing

Fatigue is a dynamic process in which the material properties of a structure progressively weaken over time under varying loads, such that the loads do not cause failure over a short duration but do cause failure over a long duration of time. The fatigue testing that was performed on the 3 types of bone cements included varying the load placed on a specimen in a periodic manner. Specifically, the fatigue tests were performed on an Instron 1321 Servohydrodraulic Testing Machine.

Fatigue testing specimens similar to a single edge notch bend disclosed in ASTM E-399(90) SENB were prepared. In particular, the specimens produced were in the shape of rectangular bars. The dimensions of the bars were 5×53×10 mm. A 1 mm notch was cut into each specimen using an ISOMET low speed saw with a diamond wafering blade. To help minimize the variations between notches, each notch was further sharpened with a disposable razor. The notch was placed generally in the middle of the specimen and was used to lower the fatigue life and to ensure the site of crack propagation within each specimen.

The specimens were placed in the testing machine such that 3 rollers were placing a load on the specimen. One roller was positioned on top of the specimen generally in the middle along its length. The 2 remaining rollers were positioned beneath the specimen and generally positioned towards opposite ends. The notch that was cut into the specimens as described above, was positioned below the top roller. During loading, when the top roller placed a load on the specimen, each bottom roller also applied a load to the specimen that was equal ½ the load of the top roller.

The loads placed on the specimens was done in a cyclic manner at each of the 3 points where the rollers were placed. In particular, the testing machine applied and maintained a sinewave load pattern. Specifically, during a load cycle, the load applied at the top roller started at 5 lbs. and sinusoidally increased to a maximum load of 22.5 lbs. After reaching the maximum, the load then sinusoidally decreased to 5 lbs. The set point of the curve was 13.75 lbs. Each bottom roller applied a simultaneous force that was equivalent to ½ the force of the top roller. The frequency of the cycle was set to 5 hertz. The loading rate and feedback signal were continuously monitored by an oscilloscope, and a counter recorded the number of cycles until failure occurred. Failure of a specimen was defined as fracture of the specimen into 2 distinct pieces.

Generally, in most fatigue tests, a majority of the total cycles to failure is spent initiating the crack. Fatigue cracks initiate at points of maximum local stress and at points of flaws. Here, the notch cut into each specimen was designed to initiate crack formation.

The following results were obtained during the tests. As shown, the cycles to failure and log of N cycles to failure were also used to compare the different bone cements.

TABLE V

FATIGUE LIFE OF ACRYLIC BONE CEMENTS

| Bone Cement | No. of Samples | Mean Cycles to Failure | Mean Log Cycles to Failure |
|---|---|---|---|
| Radiolucent Control | 12 | 46008 | 4.64 |
| Radiopaque Control | 23 | 114006 | 4.84 |
| 10% Microspheres | 17 | 255148 | 5.31 |

As shown in Table V, the addition of the microencapsulated barium sulfate to a radiolucent bone cement resulted in a significant increase in the fatigue life of the cement when compared to the radiolucent control and the radiopaque control. It is believed that the small crystalline particles of barium sulfate can effectively increase the resistance of crack propagation of a polymeric material if the barium sulfate is properly dispersed. Specifically, the barium sulfate may act as a defect that blunts and redirects crack development.

Also, it is noted that even though the mean cycles to failure was higher for the Radiopaque Control than for the Radiolucent Control, the Radiopaque Control had the lowest individual data points in the experiment. For instance, three of the Radiopaque Control samples failed after only 661 cycles, 7,322 cycles, and 17,193 cycles, respectively. The lowest data points for the Radiolucent Control samples and the 10% Microsphere samples, on the other hand, were 22,403 cycles and 77,541 cycles, respectively. The low results obtained for the Radiopaque control indicate radiopacifier clumping in the fracture region.

EXAMPLE NO. 21

Besides microencapsulating barium sulfate, zirconium dioxide was also similarly microencapsulated in polymethyl methacrylate using a solvent evaporation process.

Specifically, the organic phase was prepared by dissolving 20 grams of ground polymethyl methacrylate (HFI-7 obtained from Rohm & Haas) in 90 ml of chloroform (22 percent polymer concentration). Fifteen grams of zirconium dioxide obtained from Malinckrodt was added to the polymer solution and the resulting mixture was sonicated for 2.5 hours in a 20° C. water bath.

The aqueous phase was prepared by dissolving 2.5 grams of polyvinyl alcohol in 500 ml of water. The aqueous solution was mixed by a magnetic stir/heat plate for 2 hours at approximately 32° C. in order to fully dissolve the polyvinyl alcohol in the water.

After preparing the organic phase and the aqueous phase, the phases were combined to form an emulsion. Specifically, the aqueous phase was first introduced into a glass reactor followed by the organic phase. A high-speed stirrer was used to form the emulsion of the two immiscible solutions. Agitation at approximately 7,500 rpms for 2 hours at ambient pressure and room temperature was followed by 20 hours of continuous mixing at the same speed and at reduced pressure to evaporate the chloroform. After the solvent had evaporated, the newly formed microspheres were filtered and then sieved and allowed to air dry. The microspheres were then placed in a 20 in. Hg vacuum oven at 60° C. for complete drying.

The following results were obtained using light microscopy:

TABLE VI

CHARACTERISTICS OF PMMA MICROSPHERES CONTAINING ZIRCONIUM DIOXIDE

| Size Range of Microspheres (um) | Avg. Size (um) | Avg. Amount of Zirconium Dioxide in Microspheres (weight %) |
| --- | --- | --- |
| 1–90 | 60 | 50% |

Beside barium sulfate and zirconium dioxide, it is believed that many other radiopaque materials can be microencapsulated according to the present invention and incorporated into a bone cement. For instance, a bismuth glass is believed to be well suited for use in the present invention.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims.

What is claimed:

1. A radiopaque composition for combining with a liquid monomer to produce a bone cement, said composition comprising:

an acrylic powder capable of polymerizing and ultimately hardening when combined with a corresponding liquid monomer; and a predetermined amount of hollow microspheres, said hollow microspheres comprising a spherical wall made from a bone cement compatible polymer that dissolves in said liquid monomer, said hollow microspheres further including a radiopacifier contained within said spherical wall, said radiopacifier comprising an inorganic compound and wherein, when said hollow microspheres are combined with a liquid monomer, said bone cement compatible polymer dissolves dispersing said radiopacifier throughout a bone cement matrix, said predetermined amount of hollow microspheres being sufficient to make a bone cement made with said composition radiopaque.

2. A composition as defined in claim 1, wherein said radiopacifier is a material selected from the group consisting of metal oxides, barium salts, and bismuth glass.

3. A composition as defined in claim 1, wherein said radiopacifier comprises barium sulfate.

4. A composition as defined in claim 1, wherein said bone cement compatible polymer is a material selected from the group consisting of polymethyl methacrylate and copolymers thereof.

5. A composition as defined in claim 1, wherein said hollow microspheres have a size between about 1 micron to about 250 microns.

6. A composition as defined in claim 1, wherein said radiopacifier is present within each microsphere in an amount from about 15 percent to about 70 percent by weight.

7. A composition as defined in claim 4, wherein said bone cement compatible polymer has a weight average molecular weight between from about 30,000 to about 500,000 as determined by gel permeation chromatography.

8. A composition as defined in claim 1, wherein said radiopacifier is present within said composition in an amount from about 5 percent to about 30 percent by weight.

9. A composition as defined in claim 1, further comprising a polymerization initiator.

10. A composition as defined in claim 9, wherein said polymerization initiator comprises benzoyl peroxide.

11. A composition as defined in claim 1, wherein said spherical wall is from 1 micron to 25 microns thick.

12. An improved composition used in making a bone cement, said composition including an acrylic powder and a polymerization initiator, wherein, when said composition is mixed with a solution containing a corresponding liquid monomer, said acrylic powder polymerizes and hardens forming a resulting cement used in repairing or replacing bones and other hard tissues, said improvement comprising:

a predetermined amount of hollow microspheres added to said acrylic powder, each of said hollow microspheres comprising a thin spherical coating of a bone cement compatible material said spherical coating containing a radiopacifier therein, said radiopacifier comprising an inorganic compound, wherein, when said improved composition is combined with a corresponding liquid monomer, a predominant portion of said coating of said bone cement compatible material dissolves releasing and disbursing said radiopacifier throughout a curing bone cement matrix, said radiopacifier for creating a radiopaque bone cement and for increasing the fatigue life of said cement.

13. An improved composition as defined in claim 12, wherein said radiopacifier is a barium salt, zirconium dioxide, or a bismuth glass.

14. An improved composition as defined in claim 12, wherein said coating of bone cement compatible material is comprised of a material selected from the group consisting of polymethyl methacrylate and copolymers thereof, said coating being between 1 micron and 10 microns thick.

15. An improved composition as defined in claim 12, wherein said hollow microspheres have a size between about 5 microns to about 100 microns.

16. An improved composition as defined in claim 12, wherein said radiopacifier comprises from about 15 percent to about 70 percent by weight of each hollow microsphere.

17. An improved composition as defined in claim 12, wherein said radiopacifier is present within said composition in an amount from about 5 percent to 30 percent by weight.

18. An improved composition used in making a bone cement, said composition including an acrylic powder and a polymerization initiator, wherein, when said composition is mixed with a solution containing a corresponding liquid monomer, said acrylic powder polymerizes and hardens forming a resulting cement used in repairing or replacing bones and other hard tissues, said improvement comprising:

a predetermined amount of hollow microspheres added to said acrylic powder, each of said hollow microspheres comprising a thin spherical coating of a bone cement compatible material, said spherical coating containing a radiopacifier therein, said radiopacifier comprising an inorganic compound, wherein, when said improved composition is combined with a corresponding liquid monomer, a predominant portion of said coating of said bone cement compatible material dissolves releasing and dispersing said radiopacifier throughout a curing bone cement matrix, and wherein said coating of said bone cement compatible material has a thickness such that said coating will completely dissolve when 40 grams of said composition are combined with 20 ml of a liquid monomer and mixed for at least 2 minutes, said radiopacifier for creating a radiopaque bone cement and for increasing the fatigue life of said cement.

19. A method of dispersing a radiopacifier within a bone cement, said method comprising the steps of:

microencapsulating a radiopacifier with a wall forming polymer to form hollow radiopaque microspheres, said hollow microspheres having a spherical wall made from said wall forming polymer, said radiopacifier being contained within said spherical wall, said radiopacifier comprising an inorganic compound, said wall forming polymer being bone cement compatible;

combining said hollow microspheres with an acrylic powder, said hollow microspheres being added to said acrylic powder in an amount sufficient to make a resulting bone cement radiopaque; and contacting said hollow microspheres and said acrylic powder with a liquid monomer causing said wall forming polymer to dissolve releasing said radiopacifier into a bone cement matrix.

20. A method of dispersing a radiopacifier within a bone cement, said method comprising the steps of:

coating a radiopacifier with a wall forming polymer to form hollow radiopaque microspheres, said hollow microspheres having a spherical wall made from said wall forming polymer, said radiopacifier being contained within said spherical wall, said radiopacifier comprising an inorganic compound, said wall forming polymer being bone cement compatible;

combining said hollow microspheres with an acrylic powder, said hollow microspheres being added to said acrylic powder in an amount sufficient to make a resulting bone cement radiopaque; and contacting said hollow microspheres and said acrylic powder with a liquid monomer causing said coating of wall forming polymer to dissolve releasing said radiopacifier into a bone cement matrix, and wherein the method of coating said radiopacifier comprises the steps of:

combining said wall forming polymer and said radiopacifier with a solvent, wherein said wall forming polymer dissolves in said solvent;

blending said solvent containing said polymer and said radiopacifier with an aqueous solution to form an emulsion, said solvent being immiscible within said aqueous solution;

evaporating said solvent from said emulsion thereby forming said hollow microspheres; and separating said hollow microspheres from said remaining aqueous solution.

21. A method as defined in claim 19, wherein said radiopacifier is a barium salt, a metal oxide, bismuth glass, or mixtures thereof.

22. A method as defined in claim 19, wherein said wall forming polymer is a material selected from the group consisting of polymethyl methacrylate and copolymers thereof.

23. A method as defined in claim 20, further comprising the step of adding an emulsifier to said emulsion.

24. A method as defined in claim 20, wherein said solvent is a material selected from the group consisting of methylene chloride, chloroform, ethylene chloride and benzene.

25. A bone cement system for producing a radiopaque bone cement, said system comprising:

a liquid monomer; and a corresponding dry component composition for combining with said monomer to form a cement, said composition comprising an acrylic powder mixed with hollow microspheres, said hollow microspheres comprising a spherical wall made from a bone cement compatible polymer, said spherical wall containing a radiopacifier therein, said radiopacifier comprising an inorganic compound, wherein, when combined with said monomer, said bone cement compatible polymer dissolves dispersing said radiopacifier throughout said resulting cement in an amount sufficient to make said cement radiopaque.

* * * * *